US00PP24707P3

(12) United States Plant Patent

Klemm et al.

(10) Patent No.: US PP24,707 P3

(45) Date of Patent: Jul. 29, 2014

(54) CARNATION PLANT NAMED 'KLEDG12163'

(50) Latin Name: ***Dianthus* cultivar**
Varietal Denomination: KLEDG12163

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 113 days.

(21) Appl. No.: 13/694,210

(22) Filed: Nov. 7, 2012

(65) Prior Publication Data

US 2014/0130219 P1 May 8, 2014

(51) Int. Cl.
*A01H 5/00* (2006.01)

(52) U.S. Cl.
USPC ..... Plt./273

(58) Field of Classification Search
USPC ..... Plt./273
See application file for complete search history.

*Primary Examiner* — Kent L Bell

(74) *Attorney, Agent, or Firm* — Jondle Plant Sciences Division of Swanson & Bratschun, L.L.C.

(57) ABSTRACT

A new and distinct variety of carnation plant named 'KLEDG12163' particularly characterized by small, dark purple flowers with a lavender edge and an upright, compact growth habit, is disclosed.

1 Drawing Sheet

Genus and species: *Dianthus* cultivar.
Variety denomination: 'KLEDG12163'.

BACKGROUND OF THE NEW PLANT

The present invention comprises a new and distinct variety of carnation, botanically known as *Dianthus* and hereinafter referred to by the variety name 'KLEDG12163'. The new variety is the result of a cross conducted in May 2009 in Stuttgart, Germany between the proprietary female parent carnation plant, 'DSS 07 0016' (unpatented) and the proprietary male parent carnation plant, 'DSS 07 0020' (unpatented). A single plant selection was subsequently chosen for further evaluation and for asexual propagation.

The new variety was first propagated via vegetative cuttings in June 2010 in Stuttgart, Germany and has been asexually reproduced repeatedly by vegetative cuttings in Stuttgart, Germany for six to eight generations. 'KLEDG12163' has been found to retain its distinctive characteristics through successive asexual propagations via vegetative cuttings.

Plant Breeder's Rights for this variety have not been applied for. 'KLEDG12163' has not been made publicly available or sold anywhere in the world more than one year prior to the filing date of this application.

SUMMARY OF THE INVENTION

The following are the most outstanding and distinguishing characteristics of this new variety when grown under normal horticultural practices in a greenhouse in Stuttgart, Germany.

1. Small, dark purple flowers with a lavender edge; and
2. An upright, compact growth habit.

DESCRIPTION OF THE PHOTOGRAPH

This new carnation plant is illustrated by the accompanying photograph which shows overall plant habit including blooms, buds, and foliage of the plant. The photograph is of a five month-old plant grown in a glass covered greenhouse in Stuttgart, Germany in 2012. The colors shown are as true as can be reasonably obtained by conventional photographic procedures.

DESCRIPTION OF THE NEW VARIETY

The following detailed descriptions set forth the distinctive characteristics of 'KLEDG12163'. The data which define these characteristics were collected from asexual reproductions carried out in Stuttgart, Germany. The plant history was taken in the spring of 2012 on 5-month-old plants grown in 10 centimeter pots. The plants were grown in a glass covered greenhouse and pinched at week 45. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Caryophyllaceae.
- *Genus and species.*—*Dianthus* cultivar.
- *Common name.*—Carnation.

Parentage:
- *Female parent.*—'DSS 07 0016' (unpatented).
- *Male parent.*—'DSS 07 0020' (unpatented).

Plant:
- *Form.*—Potted plant.
- *Habit.*—Upright, compact.
- *Height.*—22.0 cm.
- *Width* (*spread*).—16.0 cm.
- *Life cycle.*—Semi-perennial.
- *Flowering habit.*—Continuous.
- *Time to produce a finished flowering plant.*—3 months.

*Propagation type.*—Vegetative cuttings.
*Time to initiate roots.*—16 days.
*Root description.*—Fine; white, RHS 155B.
*Temperature tolerances.*—Normal.

Branches:
*Quantity per plant.*—8 to 12.
*Color.*—RHS 146B.
*Length.*—5.0 cm.
*Diameter.*—2.0 cm.
*Internode length.*—0.2 cm to 1.0 cm.
*Texture.*—Smooth.

Leaves:
*Arrangement.*—Opposite.
*Shape.*—Lanceolate.
*Apex.*—Acute.
*Base.*—Obtuse.
*Margin.*—Entire.
*Color.*—Upper surface (both immature and mature leaves): RHS 146B. Lower surface (both immature and mature leaves): RHS 137C.
*Length.*—4.0 cm to 5.0 cm.
*Width.*—0.4 cm.
*Texture.*—Smooth.
*Venation.*—Absent.
*Petioles.*—Absent.

Inflorescence:
*Type.*—Small sprays.
*Flowering season.*—Spring to autumn.
*Lastingness of individual blooms on the plant.*—10 to 16 days.
*Width.*—2.0 cm.
*Depth.*—0.5 cm.
*Shape.*—Round.
*Fragrance.*—Present.
*Number of flowers per plant.*—8 to 15.
*Corolla.*—Form: Round. Length: 0.5 cm. Width (depth): 2.0 cm.
*Calyx.*—Form: Cylinder vase. Length: 1.5 cm. Width: 0.4 cm.

Flower buds:
*Color.*—RHS 137C.
*Shape.*—Elliptic.
*Length.*—0.5 cm to 1.0 cm.
*Diameter.*—0.3 cm to 0.4 cm.

Petals:
*Arrangement.*—Semi-double; arranged in several whorls.
*Quantity* (*per flower*).—5 to 10.
*Shape.*—Spoon-shaped.
*Apex.*—Obtuse.
*Base.*—Acute.
*Margin.*—Serrate.
*Length.*—1.8 cm to 2.1 cm.
*Width.*—1.0 cm to 1.2 cm.
*Color.*—When opening: Upper surface: RHS N79A and RHS N74C. Lower surface: RHS N73A. When fully opened: Upper surface: RHS N79B and RHS N74D. Lower surface: RHS N79A.
*Texture* (*both upper and lower surfaces*).—Smooth.

Sepals:
*Arrangement.*—Fused.
*Quantity* (*per flower*).—5.
*Shape.*—Elliptic.
*Apex.*—Acute.
*Base.*—Obtuse.
*Margin.*—Smooth.
*Length.*—0.8 cm.
*Width.*—0.4 cm.
*Color.*—Upper surface: RHS 137A. Lower surface: RHS 137D.
*Texture* (*both upper and lower surfaces*).—Smooth.

Peduncle:
*Length.*—5.0 cm to 8.0 cm.
*Diameter.*—0.2 cm.
*Texture.*—Smooth.
*Color.*—RHS 146B.

Reproductive organs:
*Pistils.*—Quantity: 1. Style: Length: 0.2 cm. Color: RHS N155B. Stigma color: RHS N155D. Ovary color: RHS N142D.
*Stamens.*—Quantity: Moderate. Filament: Length: 0.3 cm. Color: RHS 69D. Anther color: RHS 69C. Pollen amount: Moderate.

Fruit and seed set: None observed.

Disease and insect resistance: Good resistance to insects; medium resistance to *Alternaria*.

COMPARISON WITH PARENTAL AND COMMERCIAL VARIETIES

'KLEDG12163' differs from the female parent carnation plant 'DSS 07 0016' (unpatented) in that 'KLEDG12163' has semi-double, small, dark purple flowers with a lavender edge, whereas 'DSS 07 0016' has double, small, lavender flowers with a dark red center. Additionally, 'KLEDG12163' has an upright, compact growth habit, whereas 'DSS 07 0016' has a medium growth habit.

'KLEDG12163' differs from the male parent carnation plant 'DSS 07 0020' (unpatented) in that 'KLEDG12163' has dark purple flowers with a lavender edge and an upright, compact growth habit, whereas 'DSS 07 0020' has dark pink flowers and a medium growth habit.

'KLEDG12163' differs from the commercial carnation plant 'Mendlesham Minx' (unpatented) in that 'KLEDG12163' has dark purple flowers with a lavender edge and an upright, compact growth habit, whereas 'Mendlesham Minx' has light lavender, picoté flowers with a dark red center and a medium growth habit.

We claim:

1. A new and distinct variety of carnation plant named 'KLEDG12163' as shown and described herein.

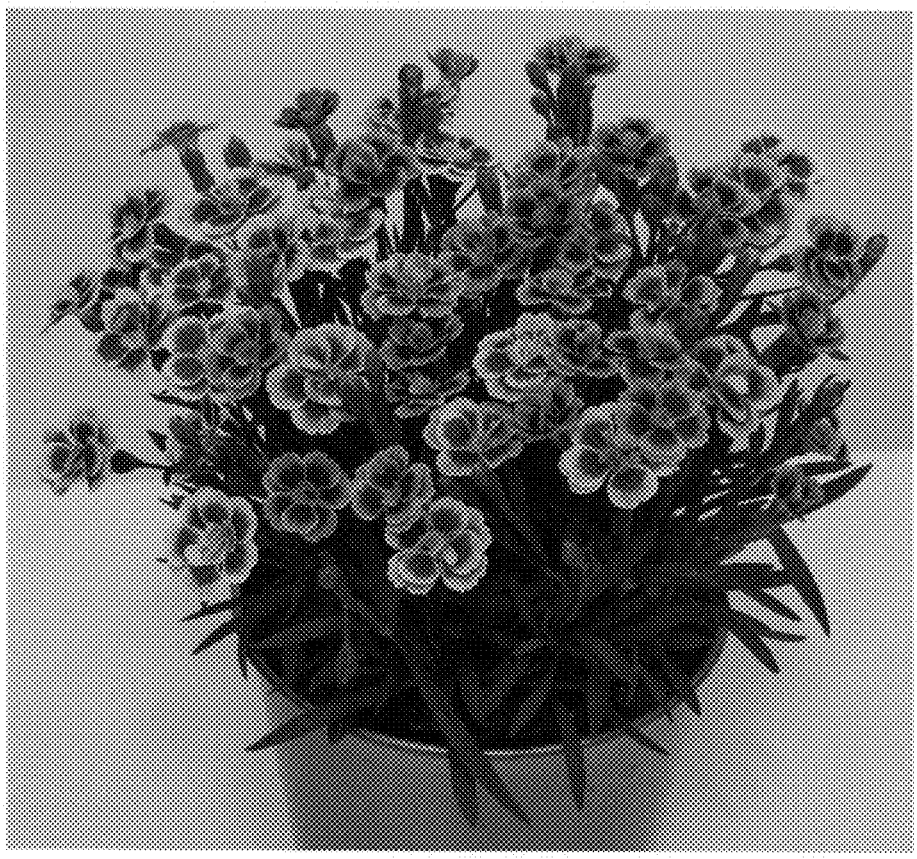

* * * * *